United States Patent
Dreisörner

(10) Patent No.: US 7,958,773 B2
(45) Date of Patent: Jun. 14, 2011

(54) METHOD FOR RAPID TESTING OF THE QUALITY OF CEREALS, GRITS AND FLOURS BY MEASURING THE AGGREGATION OF GLUTEN

(75) Inventor: Jens Dreisörner, Lübbecke (DE)

(73) Assignee: Brabender GmbH & Co. KG, Duisburg (DE)

( * ) Notice: Subject to any disclaimer, the term of this patent is extended or adjusted under 35 U.S.C. 154(b) by 32 days.

(21) Appl. No.: 12/083,174

(22) PCT Filed: Sep. 28, 2006

(86) PCT No.: PCT/DE2006/001718
§ 371 (c)(1),
(2), (4) Date: Apr. 7, 2008

(87) PCT Pub. No.: WO2007/041987
PCT Pub. Date: Apr. 19, 2007

(65) Prior Publication Data
US 2009/0266184 A1   Oct. 29, 2009

(30) Foreign Application Priority Data
Oct. 7, 2005   (DE) .................. 10 2005 048 184

(51) Int. Cl.
*G01N 11/14* (2006.01)
(52) U.S. Cl. ..................................... 73/54.31; 73/54.28
(58) Field of Classification Search .................. 73/54.28, 73/54.31–54.35
See application file for complete search history.

(56) References Cited

U.S. PATENT DOCUMENTS

| | | | | |
|---|---|---|---|---|
| 4,293,854 | A | * | 10/1981 | Gookins et al. ............... 340/615 |
| 5,513,912 | A | * | 5/1996 | Lotz et al. ..................... 366/349 |
| 6,557,397 | B2 | * | 5/2003 | Langsch ...................... 73/54.01 |

FOREIGN PATENT DOCUMENTS

| | | | |
|---|---|---|---|
| DE | 233 423 | | 2/1986 |
| DE | 198 28 667 | | 1/1999 |
| GB | 1 217 329 | | 12/1970 |
| GB | 2 326 723 | | 12/1998 |
| GB | 2326723 | A * | 12/1998 |
| JP | 05056744 | A * | 3/1993 |
| JP | 05212678 | A * | 8/1993 |
| SU | 1 392 453 | | 4/1988 |

OTHER PUBLICATIONS

Translation of JP 05056744.*
International Search Report.
Botterbrodt et al., "Qualitätsbeschreibung von Mehlen für nicht hefegelockerte Feine Backwaren (Flachwaffeln, Hartkekse, Mürbkekse) )," ["Quality description of flours for fine baked goods not loosened with yeast"] in Getreide Mehl und Brot [Grain, Flour, and Bread], Issue 52, 1998, pp. 103-109. (Spec, p. 1).
Hanneforth et al., "Mehle fur besondere Verwendungszwecke," Getreide Mehl und Brot [Grain, Flour, and Bread], Issue 51, 1997, pp. 227-231. (Spec, pp. 1-2).

* cited by examiner

*Primary Examiner* — Hezron Williams
*Assistant Examiner* — Nashmiya Fayyaz
(74) *Attorney, Agent, or Firm* — Collard & Roe, P.C.

(57) ABSTRACT

The invention concerns a method and a device for rapid testing of the quality of cereals, grits and flours by measuring the aggregation of gluten, whereby the sample to be tested in aqueous solution/suspension containing mineral salts and/or acids and/or liquors in a specific amount in a sample cup is stirred with an electrically driven stirring paddle and the resistance opposed to the paddle by the sample during the stirring process is measured, the torque loads acting on the rotatably mounted electric drive motor being measured from the beginning of the stirring process by means of extensometric gauges, the measurement being completed once the maximum rotating torque is reached and the measuring process being monitored, controlled and analyzed by software.

3 Claims, 5 Drawing Sheets

METHOD FOR RAPID TESTING OF THE QUALITY OF CEREALS, GRITS AND FLOURS BY MEASURING THE AGGREGATION OF GLUTEN

CROSS REFERENCE TO RELATED APPLICATIONS

This application is the National Stage of PCT/DE2006/001718 filed on Sep. 28, 2006, which claims priority under 35 U.S.C. §119 of German Application No. 10 2005 048 184.1 filed on Oct. 7, 2005. The international application under PCT article 21(2) was not published in English.

BACKGROUND OF THE INVENTION

1. Field of the Invention

The invention relates to a method for a rapid test of the quality of grains, crushed grains, and flours, by means of measuring the gluten aggregation.

2. Description of the Related Art

In their article "*Qualitätsbeschreibung von Mehlen für nicht hefegelockerte feine Backwaren*" ["Quality description of flours for fine baked goods not loosened with yeast"], in: *Getreide, Mehl und Brot* [Grain, Flour, and Bread] 52 (1998), 2, the authors Botterbrodt, Hanneforth, Lewandrowski, and Brümmer explain that in the description of flour quality, the questions as to what characteristic data characterize the quality, and what characteristic data possess informational value for the range of use stand in the foreground. The characteristic values of flour quality, e.g. the protein content, the wet gluten content, but also those obtained from baking experiments, such as the rapid mix test (RMT), are variables known for this purpose.

In the article, in connection with rapid testing of flours, the so-called knock-out test is mentioned, which was already described for the first time in 1997, in the journal "*Getreide, Mehl und Brot*," Issue 51, by the authors Hanneforth, Zwingelberg, and Gebhard. In this test, also known as the gluten aggregation test, the aggregation behavior of a flour/water suspension in a ratio of 1:1.2 to 1:1.5 is observed, using distilled water. The grain to be studied is brought to a certain temperature and weighed into the mixer top in a commercially available mixer (110 g, for example). The water is tempered to 23° C., for example, and also weighed into the mixer (132 g, for example).

The mixer is turned on and allowed to run at a medium level (at approximately 4500 rpm) for about 20 seconds. Then, the mixer top is scratched slightly, and subsequently the mixer is operated for another 20 seconds at the previous level. Then the mixer is stopped for a short time, and the actual measurement begins, whereby the mixer runs at a higher level (6250 rpm, for example). The measurement is recorded and the time period between start of measurement and end of measurement is determined. The end of the measurement is reached when the power consumption of 2 amperes is reached after the maximum. The goal and purpose of this test is to confirm wheat lots (e.g. of the E and A wheat groups) that have been delivered and marked accordingly, by means of a corresponding aggregation behavior.

For a determination of the time point of maximal gluten cross-linking, an ampere meter is connected with the mixer. As a result of the formation of the gluten lattice in the mass, the mixer experiences increasing resistance, which leads to increased power consumption and thus to an increase in the ampere number displayed.

However, a disadvantage in this method is the fact that identical electric motors can never be present in different devices, so that each device records different power consumption values, since different windings also bring different thermal general conditions with them.

Furthermore, the use of distilled water is not suitable for every sample, since it has been found that in the case of many samples, in the case of so-called weak flours, no aggregation takes place. A further disadvantage is the relatively large sample amount that is needed. Another decisive disadvantage, however, is the long testing time, whereby the preparatory method steps up to the start of the actual measurement are complicated and time-intensive.

SUMMARY OF THE INVENTION

The invention is therefore based on the task of conducting a rapid test of the type stated initially, in such a manner that more precise results are obtained independent of the device, with a minimized sample amount, even in the case of weak flours.

The invention accomplishes this task with the characteristics of the method according to the invention. Further advantageous embodiments of the invention are discussed below, whereby a particularly configured device is proposed for carrying out the method.

The decisive innovation as compared with the state of the art can be seen, in the method according to the invention, in that the force that occurs and is required for deformation is measured directly; this force increases slowly during aggregation, and then reaches a maximum. Thus, one is independent of thermal effects that could falsify the measurement. The torsion forces that the sample exerts, during the measurement, on the electric motor for the stirring paddle, for example, which motor is mounted so as to rotate, is transferred to the measurement devices, which works with expansion measurement strips, by way of a lever arm having a defined length. The software that accompanies the measurement process calculates the corresponding torque from the force and the known lever arm.

Alternatively, the force measurement can also take place directly, by way of the axle or the rotation of the beaker that is alternatively mounted to as to rotate.

DETAILED DESCRIPTION OF THE PREFERRED EMBODIMENTS

Figure 4:
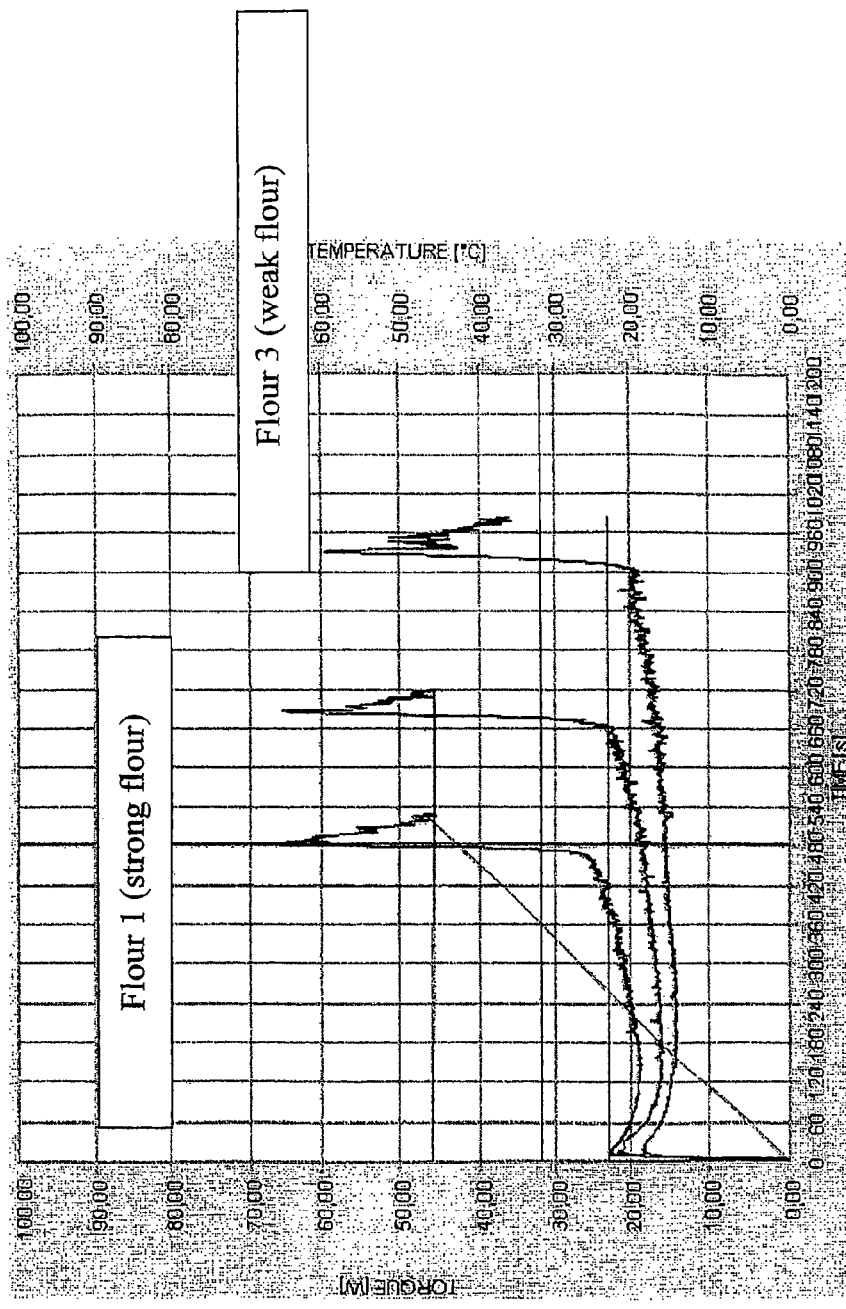
FIG. 4 is a diagram showing measurement procedures for three different types of flour.

In FIG. 4, the measurement procedures for three different types of flour are shown, whereby a so-called strong flour, a so-called weak flour, and a flour that lies between the two were tested.

As is evident from this diagram, the strong flour already reaches the maximum after 480 seconds, while the weak flour has reached the aggregation maximum only after slightly more than 900 seconds.

Using the method according to the invention, it is therefore possible to differentiate different flours on the basis of their maxima.

Figure 3:
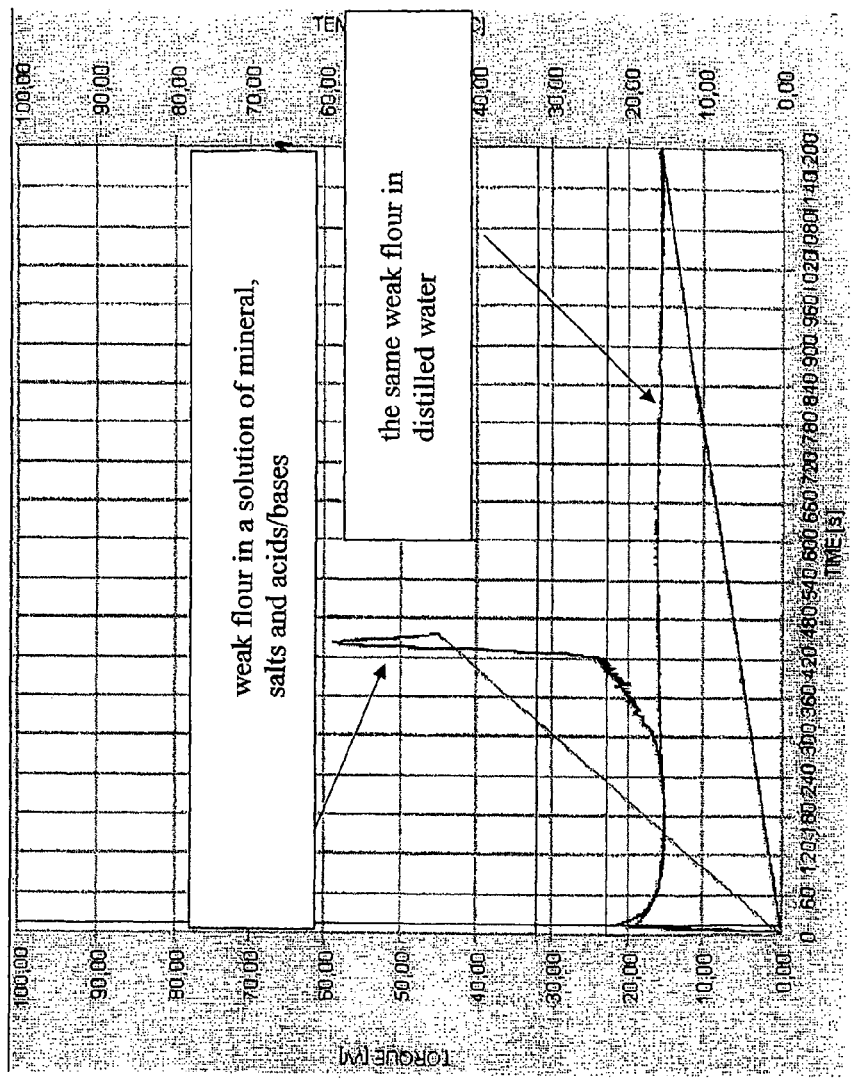
FIG. 3 is a diagram showing differentiation by means of a suspension medium.

In FIG. 3, it is shown that the aggregation behavior even of a weak flour can be verified using the method according to the invention, by means of the use of a solution of mineral salts and acids/bases, whereby here, the maximum is reached at an aggregation time of about 430 seconds. In contrast, the diagram for the same weak flour in distilled water (as in the state of the art) does not show any aggregation behavior.

In summary, it can be stated that using the method according to the invention, it is possible to reliably test the most varied flours, crushed grains, grains, and also baking mixtures with regard to their aggregation behavior.

For this purpose, in contrast to the state of the art, only a small test amount is needed. Experiments have shown that at a ratio of material to be tested and sample solution between 1:1.2 and 1:1.5, sample amounts of 10 to 20 g and solution amounts of approximately the same size are sufficient.

According to an embodiment, the suspension medium should have a conductivity of >5 µS and a pH<2 to 13.

According to an embodiment, it is provided that the speed of rotation of the measurement paddle is not supposed to exceed 6000 rpm. This is gentler for the sample, for one thing, and also gentler for the device, for another thing.

The speed of rotation, which can also be significantly lower than 6000 rpm (between 1000 and 6000 rpm), is predetermined by the software and automatically corrected by means of a constant comparison of the reference values and actual values.

In the evaluation, the temperature, which is continuously recorded, is also taken into consideration.

A preferred device for carrying out the method indicated above is discussed below. This is a device in which the drive and the measurement paddle are disposed above the sample beaker, so that the measurement paddle can be moved into the sample beaker from above. The electric motor that serves as the drive for the measurement paddle is mounted so as to rotate and connected with the force measurement device by means of a lever arm. The force measurement device works with expansion measurement strips. The torsion force exerted by the sample on the measurement paddle and from there on the electric motor is transferred to the expansion measurement strips by way of the lever arm. The corresponding torque is then calculated by the software, by forming the product of force and lever arm. The new geometry of the sample beaker and of the measurement paddle is particularly advantageous; this is because they are optimally coordinated with one another in terms of their shape. The measurement beaker has a smooth wall and is configured in cylinder shape. The outline of the measurement paddle is rectangular, and essentially agrees with the longitudinal cross-section of the smooth-walled stirring beaker. Recesses that are open to the outside are provided in the longitudinal side walls of the measurement paddle, allowing the stirred sample to pass through. Recesses are also provided in the inside surface of the measurement paddle.

The sample beaker, which has a simple structure in this manner, is preferably held on the device with a bayonet closure, and can consist of coated sheet steel or also of plastic.

The measurement paddle is also characterized by its simple, inexpensive structure.

A brushless motor, whose speed of rotation can be stabilized electronically, is proposed as a drive, whereas in the state of the art, alternating current motors with carbon brushes were used, in which the speed of rotation has to be manually adjusted by way of potentiometers, and thus no controlled regulation of the speed of rotation by means of an actual value/reference value comparison is possible during the measurement.

The measurement can begin immediately, without the preparatory actions described above, as soon as the measurement paddle has started to move.

Figure 1:
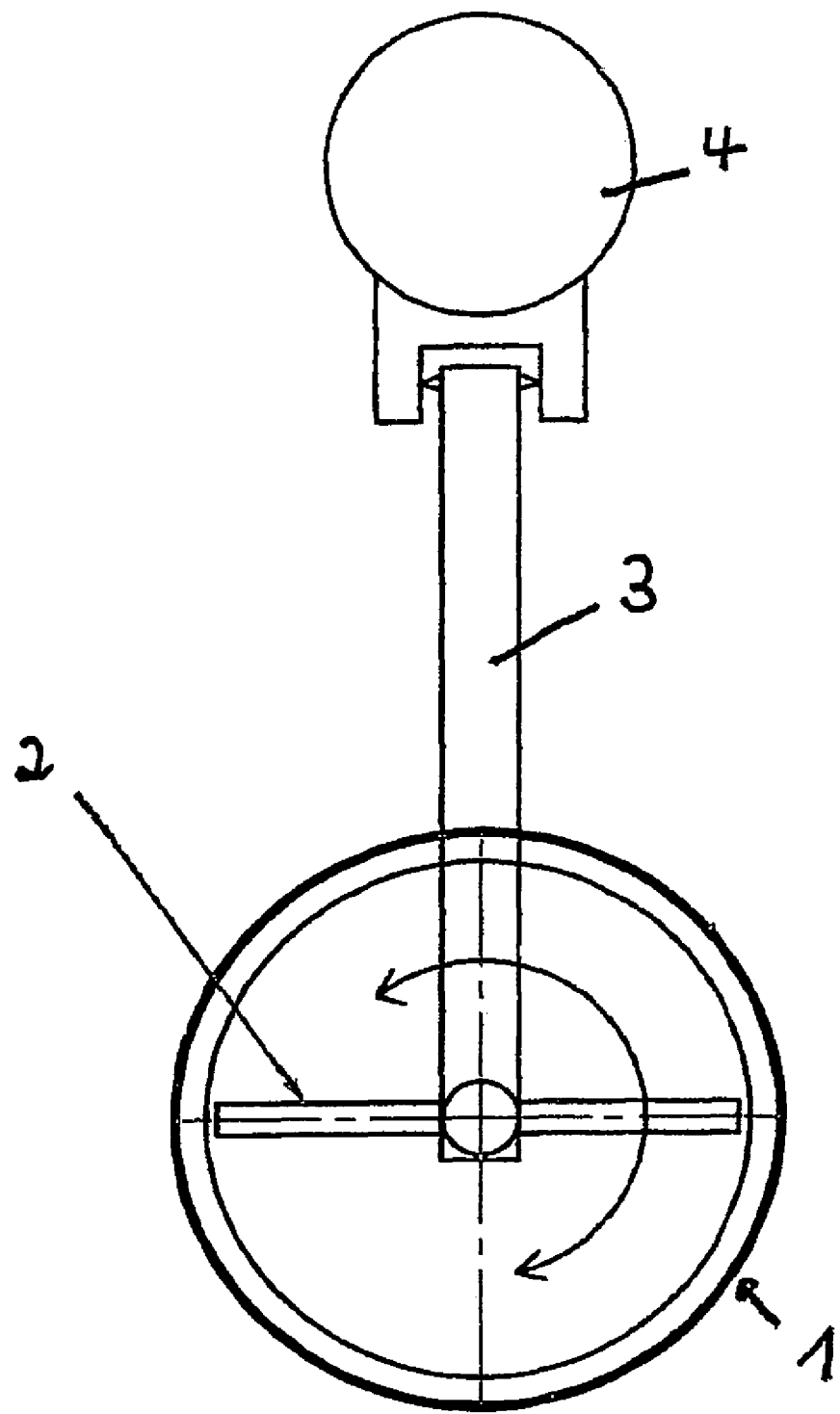
FIG. 1 shows a device for carrying out the method according to the invention.

FIG. 1 shows the schematic structure of the device for carrying out the method according to the invention.

Figure 6:
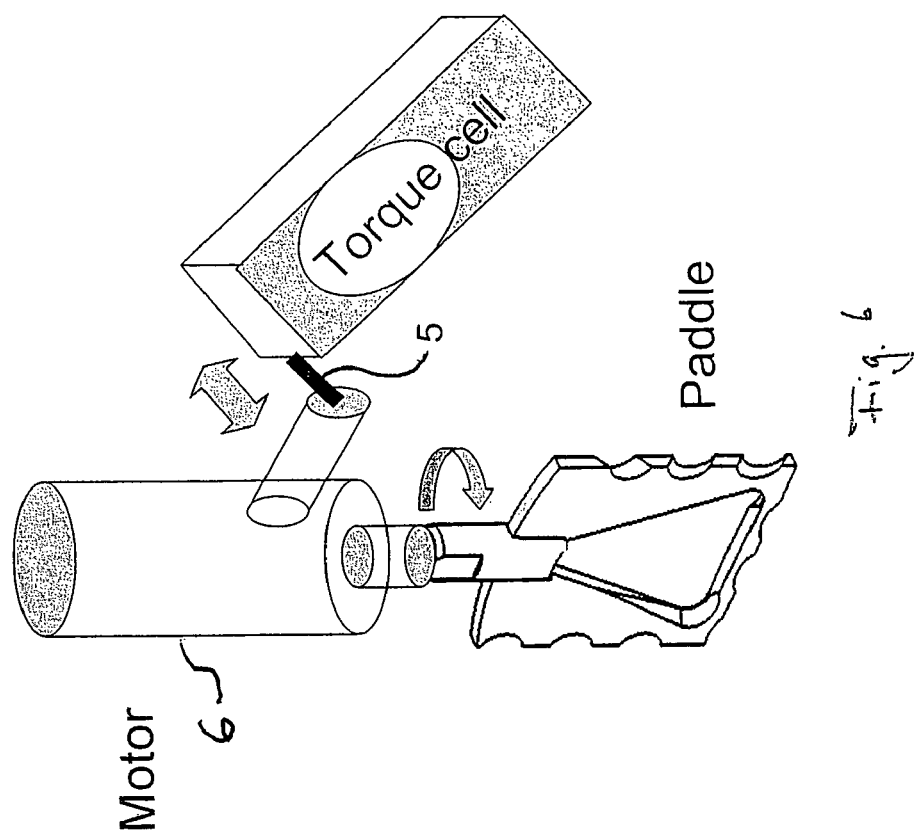
FIG. 6 shows the motor driving the measurement paddle and the measurement strips used in the method according to the invention.
Figure 5:
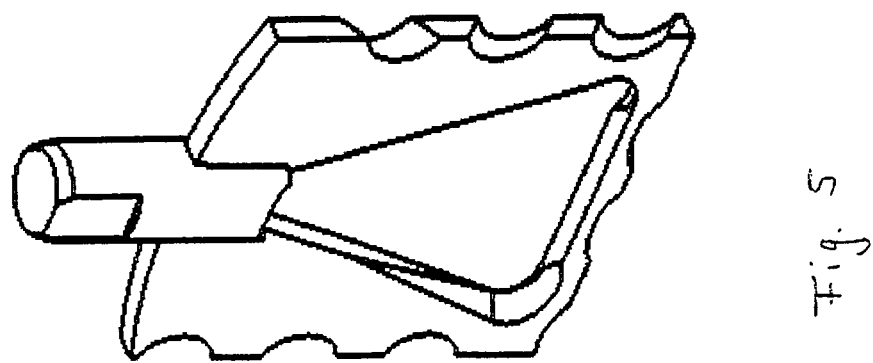
FIG. 5 shows a measurement paddle used in the method according to the invention.

The reference symbol 1 refers to the smooth-walled cylindrical sample beaker, in which a stirring measurement paddle 2 rotates. The measurement paddle 2 shown in FIG. 5 is driven by an electric motor 6, shown in FIG. 6, which is situated above the sample beaker 1. This electric motor 6 is mounted so as to rotate, and is connected with a measurement device 4 equipped with expansion measurement strips 5, by way of a lever arm 3. The force measured by the expansion measurement strips 5 is the torsion force that is produced by the resistance with which the sample counters the measurement paddle. The software calculates the corresponding torque from this force exerted on the measurement strips 5 and the defined length of the lever 3, and displays this in the diagram as a function of the running time.

Figure 2:
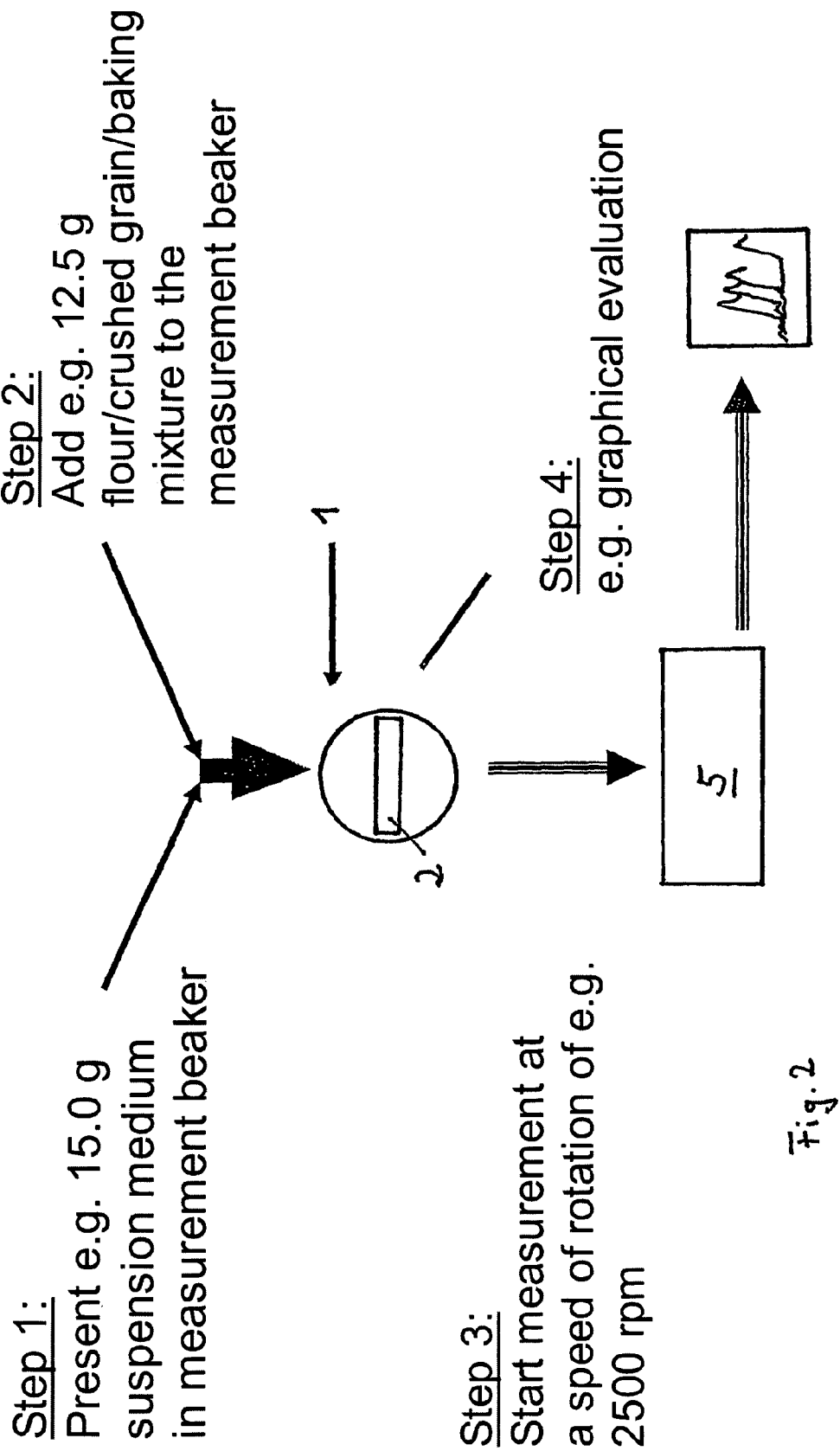
FIG. 2 is a flow schematic showing the method according to the invention.

FIG. 2 shows the flow schematic of the method according to the invention.

In the first step, the suspension medium (aqueous solution with salts, bases, acids) is introduced into the sample beaker 1. The amount is 15 g, for example. In the second step, the flour, crushed grain, baking mixture to be tested is introduced into the sample beaker 1. The amount is 12.5 g, for example. In the third step, the measurement begins with the start of the measurement paddle 2 at a speed of rotation of 2500 rpm, for example. The force is now measured, the corresponding torque is calculated from it, and in the fourth step, it is evaluated graphically. This is done by way of software that runs on the computers.

The invention claimed is:

1. A method for a rapid test of quality of a sample of grains, crushed grains, or flours, by measuring gluten aggregation, the method comprising the following steps:
   (a) stirring the sample in an aqueous solution/suspension with at least one of mineral salts, acids, and bases in a defined amount in a sample beaker using an electrically driven stirring paddle driven by an electric motor mounted to rotate at a speed of rotation between 1000 and 6000 rpm, the sample forming a suspension with the aqueous solution/suspension, the suspension formed with the sample remaining throughout an entire duration of the stirring, the stirring occurring at a single stabilized speed of rotation between 1000 and 6000 rpm throughout the entire duration of the stirring, and the electrically driven stirring paddle being a flat metal plate with a profile; and
   (b) measuring resistance with which the sample counters the stirring paddle during the stirring by measuring torsion forces acting on the electric motor by way of extensometric gauges, the measuring of torsion forces starting from commencement of the stirring and ending when a torque maximum is reached, the measuring of torsion forces being monitored, controlled, and evaluated using software, and the evaluation via software providing a quality of the sample and being based on the single torque maximum;

wherein a ratio of the sample to the aqueous solution/suspension lies between 1:1.2 and 1:1.5.

2. The method according to claim 1, wherein the speed of rotation of the electric motor is predetermined by the software and automatically corrected via constant comparison of reference values with actual values.

3. The method according to claim 1, wherein the aqueous solution/suspension is prepared with a suspension medium having a conductivity >5 μS and a pH <2 to 13.

* * * * *